United States Patent
Li et al.

(10) Patent No.: US 11,987,565 B1
(45) Date of Patent: May 21, 2024

(54) METHOD AND APPARATUS FOR TETRAHYDROCANNABINOL (THC) REMOVAL FROM HEMP EXTRACTS VIA OXIDATION

(71) Applicant: HempRise, LLC, Jeffersonville, IN (US)

(72) Inventors: Yebo Li, Powell, OH (US); Lu Zhang, Jeffersonville, IN (US)

(73) Assignee: HempRise, LLC, Jeffersonville, IN (US)

( * ) Notice: Subject to any disclaimer, the term of this patent is extended or adjusted under 35 U.S.C. 154(b) by 0 days.

(21) Appl. No.: 17/872,406

(22) Filed: Jul. 25, 2022

Related U.S. Application Data

(60) Provisional application No. 63/225,721, filed on Jul. 26, 2021.

(51) Int. Cl.
*C07D 311/80* (2006.01)

(52) U.S. Cl.
CPC .................................. *C07D 311/80* (2013.01)

(58) Field of Classification Search
CPC ................................................... C07D 311/80
See application file for complete search history.

(56) References Cited

U.S. PATENT DOCUMENTS

| | | |
|---|---|---|
| 9,867,859 B2 | 1/2018 | Raderman |
| 2018/0027192 A1 | 9/2018 | Kariman |

OTHER PUBLICATIONS

Dussy et al. Isolation of delta 9-THCA-A from hemp and analytical aspects concerning the determination of delta 9-THC in cannabis products. Forensic Science International, vol. 149, pp. 3-10. (Year: 2005).*
An, D. et al. "Targeting cannabinoid receptors: Current status and prospects of natural products." Int. J. Mol. Sci. 2020, 21(14): 5064.
Anand, P. et al. "Targeting CB2 receptors and the endocannabinoid system for the treatment of pain." Brain Res. Rev. 2009, 60(1): 255-266.
Cristino, L., et al. "Cannabinoids and the expanded endocannabinoid system in neurological disorders." Nat. Rev. Neurol. 2020, 16(1): 9-29.
Guindon J., Hohmann A.G. "The endocannabinoid system and cancer: Therapeutic implication." Br. J. Pharmacol. 2011, 163(7): 1447-1463.
Hanuš, L.O. et al. "Phytocannabinoids: A unified critical inventory." Nat. Prod. Rep. 2016, 33(12): 1357-1392.
Herlopian, A. et al. "Cannabidiol in treatment of refractory epileptic spasms: An open-label study." Epilepsy Behav. 2020, 106: 106988.
Hess, E.J. et al. "Cannabidiol as a new treatment for drug-resistant epilepsy in tuberous sclerosis complex." Epilepsia. 2016, 57(10): 1617-1624.
Koutchma, T. "UV light for processing foods." Ozone Sci. Eng. 2008, 30(1): 93-98.
McGuire, P. et al. "Cannabidiol (CBD) as an adjunctive therapy in schizophrenia: A multicenter randomized controlled trial." Am. J. Psychiatry. 2018, 175(3): 225-231.
Nagarkatti, P. et al. "Cannabinoids as novel anti-inflammatory drugs." Future Med. Chem. 2009, 1(7):1333-1349.
Nichols, J.M., Kaplan, B.L.F. "Immune responses regulated by cannabidiol." Cannabis Cannabinoid Res. 2020, 5(1): 12-31.
Pertwee, R.G. et al. "International union of basic and clinical pharmacology. LXXIX. Cannabinoid receptors and their ligands: Beyond $CB_1$ and $CB_2$." Pharmacol. Rev. 2010, 62(4), 588-631.
Pertwee, R.G. "Cannabinoid pharmacology: The first 66 years." Br. J. Pharmacol. 2006, 147(Suppl 1), S163-S171.
Reithmeier, D. et al. "The protocol for the cannabidiol in children with refractory epileptic encephalopathy (CARE-E) study: a phase 1 dosage escalation study." BMC Pediatr. 2018, 18(1): 221.
Ross, S.A., Elsohly, M.A. "Cannabinol and Δ9-THC concentration ratio as an indicator of the age of stored marijuana samples." UNPDC Data and Analysis Bulletin. 1999.
Wang, M. et al. "Decarboxylation study of acidic cannabinoids: A novel approach using ultra-high-performance supercritical fluid chromatography/photodiode array-mass spectrometry." Cannabis Cannabinoid Res. 2016, 1(1): 262-271.
Zou, S., Kumar, U. "Cannabinoid receptors and the endocannabinoid system: Signaling and function in the central nervous system." Int. J. Mol. Sci. 2018, 19(3): 833.

* cited by examiner

*Primary Examiner* — Sikarl A Witherspoon
(74) *Attorney, Agent, or Firm* — Westman, Champlin & Koehler, P.A.; Z. Peter Sawicki; Amanda M. Prose

(57) ABSTRACT

A method of oxidizing Δ9-tetrahydrocannabinol (Δ9-THC) in hemp oil to cannabinol (CBN) uses a heated spray system assisted with ultraviolet (UV) lights. The method includes heating the hemp oil to keep the hemp oil flowing freely in the heated spray system. Δ9-THC to CBN is converted by forming droplets in the presence of oxygen and the UV lights.

10 Claims, 2 Drawing Sheets

METHOD AND APPARATUS FOR TETRAHYDROCANNABINOL (THC) REMOVAL FROM HEMP EXTRACTS VIA OXIDATION

CROSS-REFERENCE TO RELATED APPLICATION(S)

This application claims the benefit of priority pursuant to 35 U.S.C. § 119(e) to U.S. provisional Application No. 63/225,721, filed Jul. 26, 2021, the entire contents of which are incorporated by reference as if fully set forth herein.

FIELD OF THE DISCLOSURE

This disclosure relates to a method for the oxidation of Δ9-tetrahydrocannabinol (Δ9-THC) in hemp extract to cannabinol (CBN).

BACKGROUND OF THE INVENTION

Cannabinoids

Cannabis refers to a group of plants known as *Cannabis sativa* L. and *Cannabis indica*. *Cannabis sativa* grows commonly in North America, Europe, and Asia, which are tall, branched, used mainly for fiber and seed, and also medicine at low Δ9-tetrahydrocannabinol (Δ9-THC) content. Compared to *Cannabis sativa*, *Cannabis indica* are short, densely branched with firm stem, broad leaflets, and high Δ9-THC content. Hemp or industrial hemp refers to the non-intoxicating (less than 0.3% Δ9-THC) varieties of *Cannabis sativa* L.

Hemp contains many chemically active compounds such as cannabinoids, terpenoids, and flavonoids. Out of over 100 cannabinoids identified so far, the most common cannabinoids in hemp are cannabidiol (CBD), cannabigerol (CBG), cannabinol (CBN), cannabichromene (CBC), cannabidivarin (CBDV), and Δ9-THC.

Cannabinoids are classified into neutral cannabinoids and acidic cannabinoids. In fresh plants, acidic cannabinoids are dominant. Geranyl pyrophosphate and olivetolic acid combine to produce cannabigerolic acid (CBGA), which is the sole intermediate for all other phytocannabinoids. After a series of reactions with specific synthases, CBGA is transformed into the acid form of the three main cannabinoids (CBDA, THCA, and CBCA). Tetrahydrocannabinolic acid (THCA) is produced from CBGA via the enzyme THCA-synthase; cannabidiolic acid (CBDA) is produced from CBGA by the enzyme CBDA-synthase; cannabichromenic acid (CBCA) is produced from CBGA via the enzyme CBCA-synthase.

The formation of major acidic cannabinoids and neutral cannabinoids from *Cannabis sativa* L. are illustrated below:

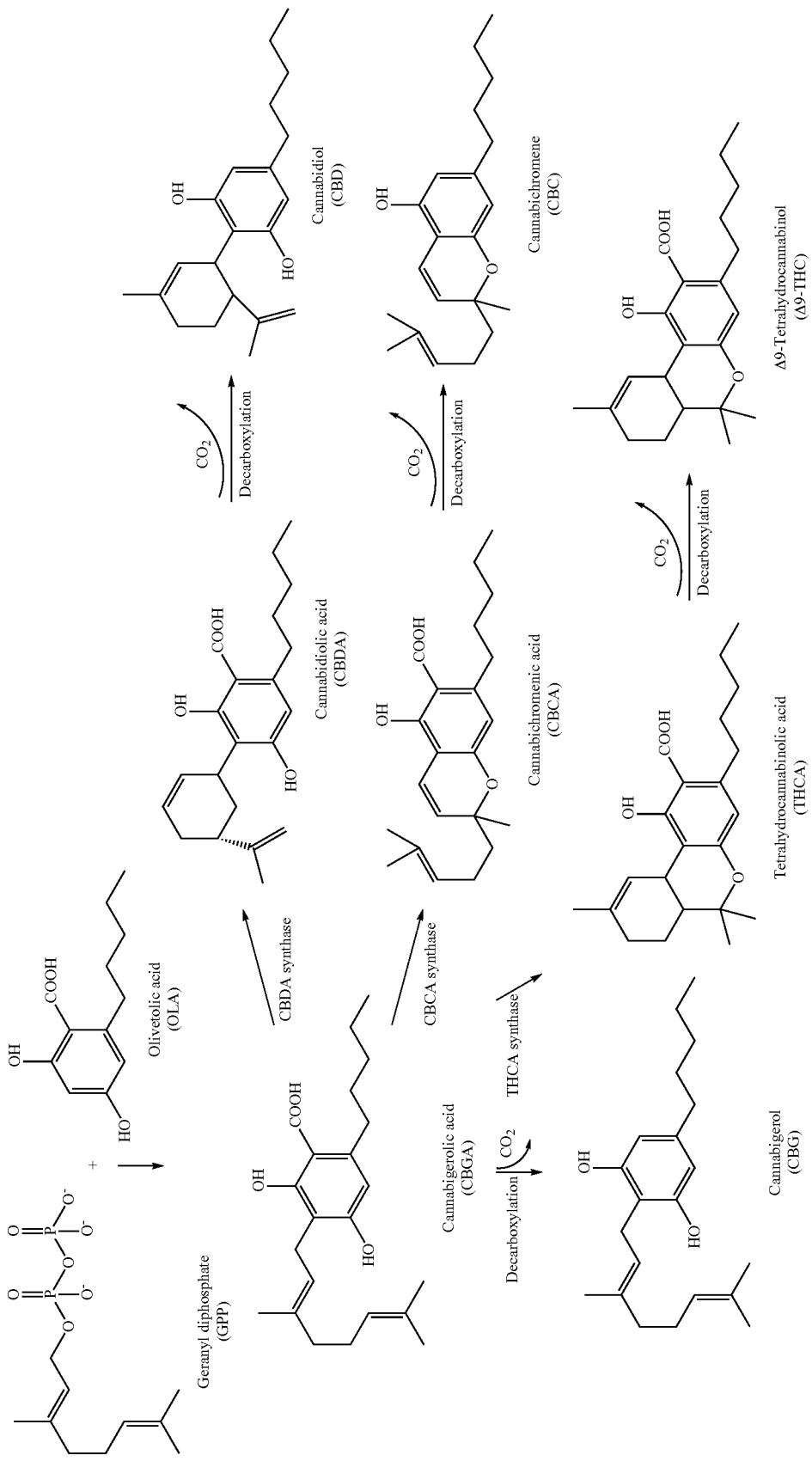

Formation of Major Acidic Cannabinoids and Neutral Cannabinoids from *Cannabis sativa* L.

The rapid transformation of CBGA to CBDA and THCA explains the low CBGA content in cannabis plants. Different strains of hemp vary in the relative proportions of CBD and THC and the risk of psychotic symptoms. Neutral cannabinoids are derived from their acidic precursors by decarboxylation. Decarboxylation is a heating process where acidic cannabinoids lose a $CO_2$ molecule and turn into their neutral form (THC, CBD and CBC). Cannabinoids are involved in a variety of physiological and pathological conditions, including inflammation, immunomodulation, analgesia, and cancer (Guindon et al., 2011).

The endocannabinoid system consists of cannabinoid receptors (CB1 and CB2), endogenous cannabinoids, as well as transport proteins and enzymes that synthesize and degrade the endocannabinoids. The endocannabinoid system is involved in a plethora of biological functions ranging from brain development and organogenesis, metabolism and food behavior, mood and anxiety, pain perception and modulation, and inflammation to the regulation of cognition, stress responses, and positive as well as negative effects (Cristino et al., 2020, Anand et al., 2009). Both CB1 and CB2 are G protein-coupled receptors affecting c-AMP. The CB1 receptor is more pervasive throughout the body with a predilection to nociceptive areas of the central nervous system and spinal cord (Zou et al., 2018), while the CB2 receptor is mostly found in the peripheral nervous system, especially immune cells, and play an important role in modulation of pain and inflammatory processes. Only Δ9-THC, its isomer Δ8-THC, and, to a lower extent, their aromatized derivative CBN bind with significant affinity to the ligand recognizing site of the CB1 and CB2 receptors (Pertwee et al., 2010). CBN only has a weak affinity for CB1 and CB2, which is about 10% of THC (Hanuš et al., 2016). The beneficial effects of the cannabinoids are mediated by multiple targets, thus not solely the cannabinoid receptors, CB1 and CB2 (An et al., 2020). Structures of cannabinoid ligands sensitive to cannabinoid receptors are shown below:

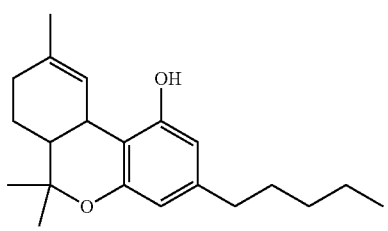

Δ9-tetrahydrocannabinol
(Δ9 THC)

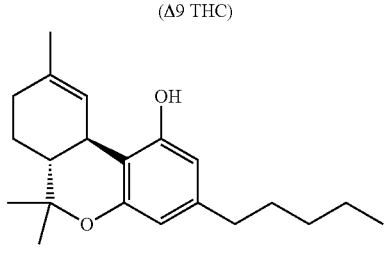

Δ8-tetrahydrocannabinol
(Δ8 THC)

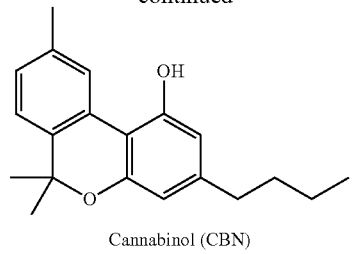

Cannabinol (CBN)

Cannabinoid Ligands Sensitive to Cannabinoid Receptors

CBD is the most abundant non-psychoactive cannabinoid of *Cannabis sativa* L., CBD has been demonstrated as a clinically interesting compound for its therapeutic potential in several disorders, including anti-inflammatory, analgesic, anti-anxiety, and antitumor properties (An et al., 2020, Nagarkatti et al., 2009, Nichols et al., 2020). Given its efficacy and promising results in animal models coupled with its safety, non-euphoric, non-psychoactive properties, and low potential for abuse, CBD is currently undergoing clinical trials for its effectiveness in schizophrenia (McGuire et al., 2018), refractory epileptic encephalopathy (Reithmeier et al., 2018), and tuberous sclerosis (Herlopian et al., 2020, Hess et al., 2016).

CBN is formed from Δ9-THC by degradation during the storage of harvested *cannabis* other than the metabolism of the plant (Pertwee, 2006). Δ9-THC can be oxidized to CBN with oxygen and light during the THCA decarboxylation process (Wang et al., 2016). CBN is a very weakly psychotropic cannabinoid whose effect is only measurable after intravenous administration. CBN shows significant sedative, anticonvulsant, anti-inflammatory, and antibiotic activities (Kariman, 2018).

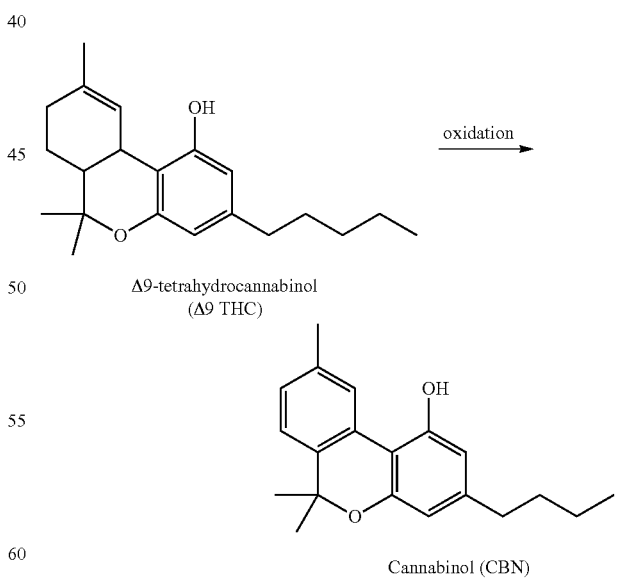

Oxidation of Δ9-THC to CBN

Ultraviolet (UV) light is non-ionizing and shortwave (200-400 nm) energy that is divided into three segments:

UV-C (200-280 nm), UV-B (280-320 nm), and UV-A (320-400 nm). The use of UV light is well established for air disinfection and surface decontamination. UV light has considerable promise to reduce the levels of microbial contamination for a wide range of liquid foods and beverages.

Due to the presence of color compounds, organic solutes, and suspended matter, liquid foods such as fresh juice products and beverages transmit relatively little UV light, and this low transmission lowers the performance efficiency of the UV light pasteurization processes. Hemp oil is a high viscosity and dark color fluid or is in solid form at room temperature. Most of the existing UV reactors have limitations for the oxidation of Δ9-THC.

Proper UV light reactor design should reduce the interference of high UV light absorbance and viscosity associated with products and therefore improves its efficiency. The flow pattern inside the UV light reactor strongly influences the total applied UV light dose, thus affecting the efficiency of the treatment (Koutchma et al., 2008). Currently, different continuous flow UV light reactor designs are being evaluated for use in the food industry for pasteurization, but none of them are suitable for processing hemp oil due to the unique properties of hemp oil.

A desirable design for UV light reactors is to provide every element of liquid that resides in the reactor for the same time period, and all materials would receive an equivalent UV light dose. However, it is important to recognize that treatment of some solids, or high viscosity fluids, or fluids with pulp will be incompatible with some of the reactor designs.

CBN forms as the oxidative byproduct of Δ9-THC (Hanuš et al., 2016, Ross et al., 1999). Studies have shown that Δ9-THC oxidation occurs at a rate of up to 5% loss per month at room temperature (Hanuš et al., 2016). However, the rate of CBN formation is not equal to the oxidative degradation rate of Δ9-THC. This seemingly missing Δ9-THC could be explained due to the proposed presence of hydroxylated and epoxidized intermediates generated during the Δ9-THC oxidation process (Hanuš et al., 2016). Additionally, the formation of Δ8-THC may account for part of the Δ9-THC loss as it can also be generated from Δ9-THC oxidatively (Hanuš et al., 2016).

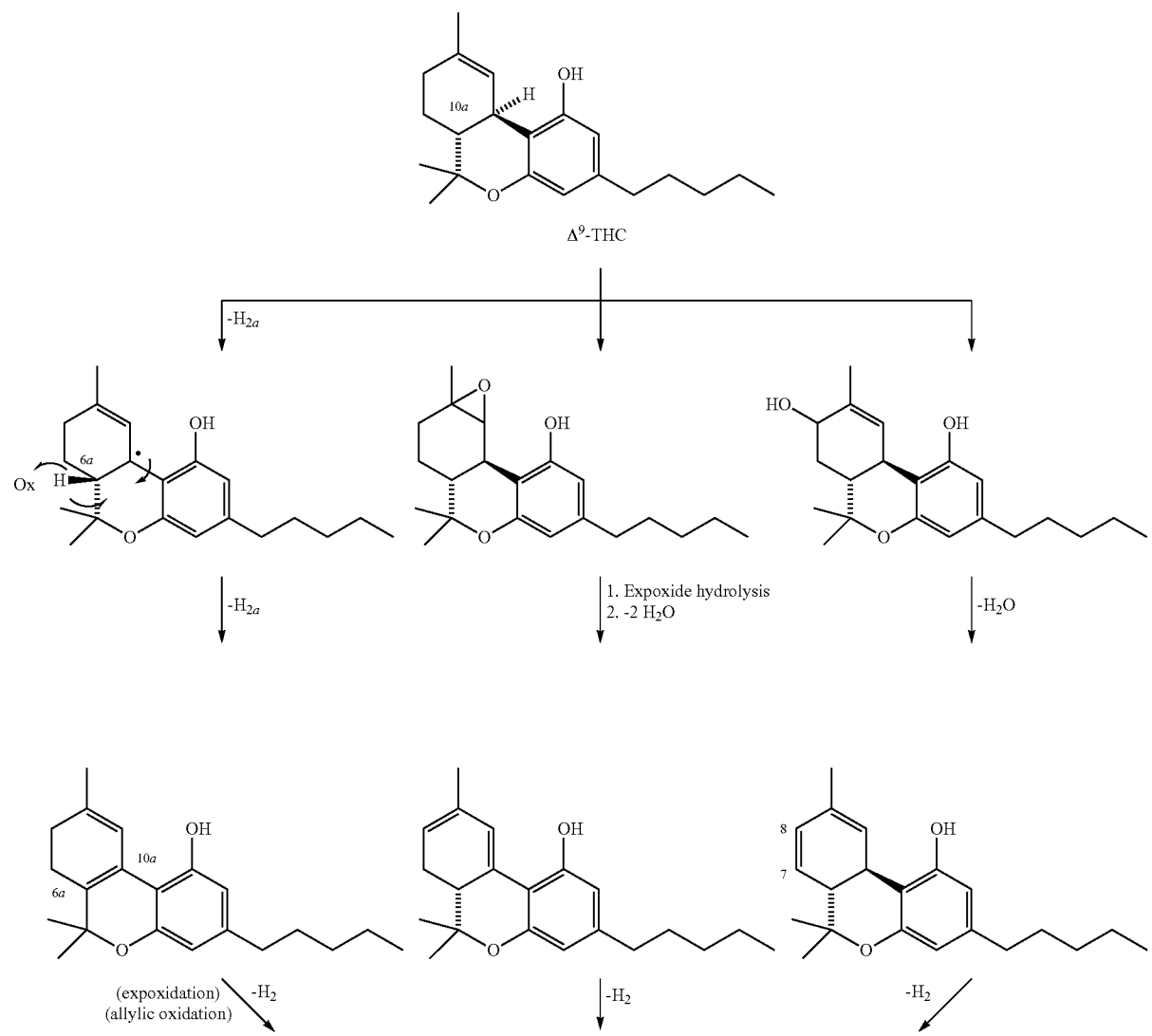

-continued

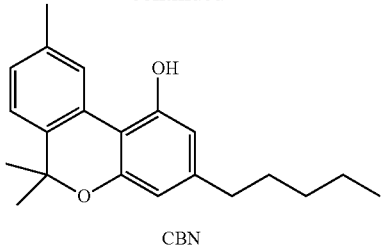

CBN

Pathway for Δ9-THC Degradation to CBN (Hanuš et al., 2016)

U.S. Pat. No. 9,867,859B2 discloses a method for modifying CBN to trans-Δ9-THC content in a lipid-based extract of cannabis to yield a low-THC product. The method includes providing a lipid-based extract of cannabis containing THC, heating the lipid-based extract at 1 atm of pressure to 157° C. to 160° C. to vaporize a first portion of the THC, and converting a second portion of the THC to CBN by heating the lipid-based extract to between 130° C. and 150° C. for at least 10 min. In one embodiment, the step of vaporizing occurs after the step of converting to remove the trans-Δ9-THC from the product.

BRIEF SUMMARY OF THE INVENTION

This disclosure describes a method of oxidizing Δ9-tetrahydrocannabinol (Δ9-THC) in hemp oil to cannabinol (CBN) in a heated spray system assisted with ultraviolet (UV) lights. The method includes heating the hemp oil to keep the hemp oil flowing freely in the heated spray system. Δ9-THC to CBN is converted by forming droplets with particle sizes about 100-500 microns in a chamber in the presence of air containing oxygen and the UV lights. The hemp oil is recirculated from and back to the chamber for further exposure to the air containing oxygen and the UV lights.

In another embodiment, the Δ9-THC content in hemp oil after oxidation is approximately 0.5% by weight or less.

In another embodiment, the step of converting uses heat to assist oxidizing Δ9-THC to CBN.

In another embodiment, the step of converting uses oxygen to oxidize Δ9-THC to CBN.

In another embodiment, the step of converting uses UV lights to expedite the oxidization of Δ9-THC to CBN.

In another embodiment, the step of converting Δ9-THC to CBN, utilizes pressurized air at approximately 5-30 PSI to form the hemp oil into droplets between approximately 100 microns and 500 microns.

In another embodiment, the step of converting Δ9-THC to CBN continues for approximately four to seven days.

In another embodiment, the hemp oil is heated to between about 55° C. and 100° C. for recirculating the hemp oil.

In another embodiment, the UV lights comprise UV-A, UV-B, UV-C, or any combination thereof.

In another embodiment, the heated hemp oil is formed into approximately 100-500 micron droplets via a nozzle with the pressurized air at approximately 5-30 PSI.

BRIEF DESCRIPTION OF THE DRAWINGS

Various features of the invention will become apparent from the following description when taken in conjunction with the accompanying drawings wherein.

DETAILED DESCRIPTION OF THE INVENTION

This disclosure describes a method for the oxidation of Δ9-tetrahydrocannabinol (Δ9-THC) in hemp extract to cannabinol (CBN). With the system of this disclosure, Δ9-THC-remediated hemp oil rich in CBD and minor cannabinoids is obtained. No solvent is used in this invention, making it a green process.

Figure 1:
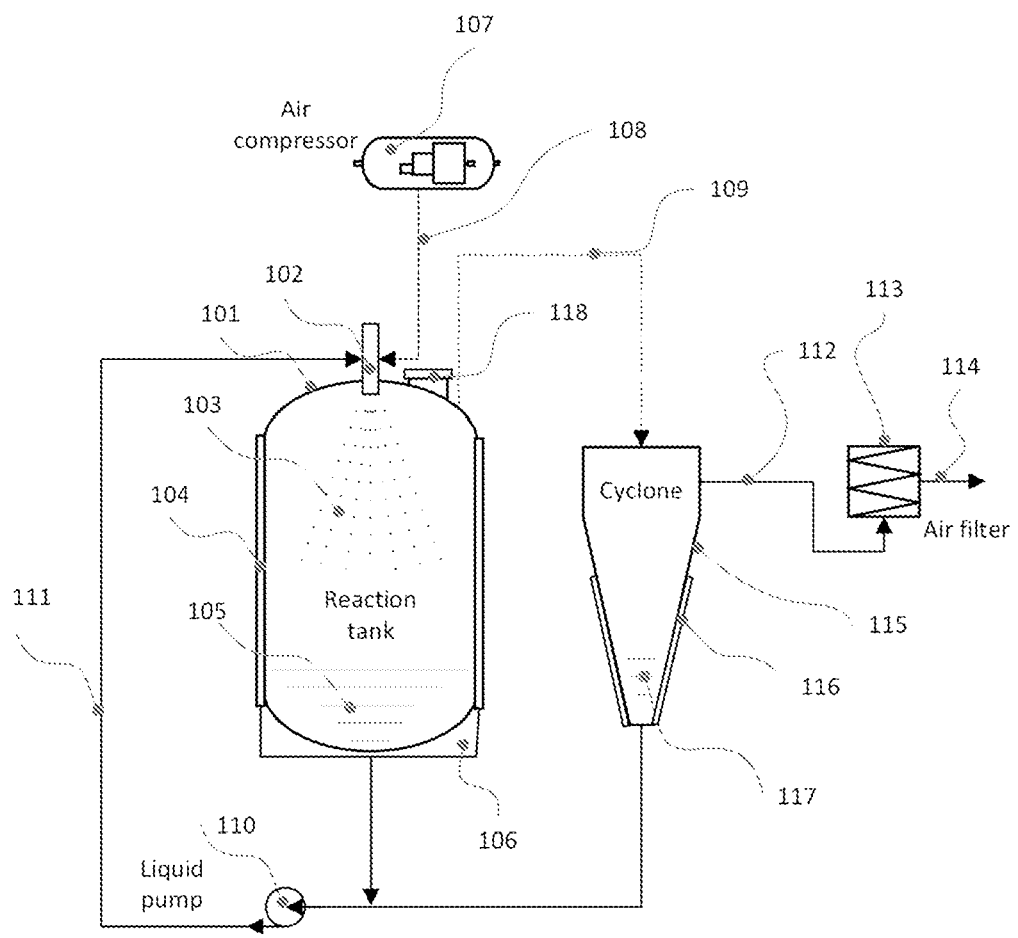
FIG. 1 is a schematic view of a batch Δ9-THC oxidation system of this disclosure.

Referring now to FIG. 1, wherein the showings are for purposes of illustrating one embodiment of the invention and not for purposes of limiting the same.

A first embodiment of the invention shown in FIG. 1 is a batch system that converts Δ9-THC to CBN. The system, detailed in FIG. 1, is fabricated from stainless steel, glass, or any other suitable material. In this embodiment, reaction tank 101 is heated with a heating jacket 106. The reaction tank may be heated with other methods such as, but not limited to, infrared, microwave, or in a heated chamber. The hemp oil 105 in the feeding tank 101 is maintained at a temperature above approximately 60° C. and circulated with a liquid pump 110 to a nozzle 102 at the top of the reaction tank. The pipeline used to circulate the hemp oil is heated with a heating jacket, blanket, or other methods to keep the hemp oil flowing freely. Compressed air 108 supplied by an air compressor 107 meets the hemp oil in the nozzle 102, where the hemp oil is atomized and jetted into fine droplets 103. In this embodiment, the air pressure is approximately 5-30 PSI. In this embodiment, the wall of the reaction tank is made of glass which is transparent to ultraviolet (UV) light 104. The UV light has maximized contact with the fine hemp oil droplets 103 in the reactor. The nozzle also provides full contact of air/oxygen with the hemp oil to expedite the oxidation process. In this embodiment, the hemp oil 105 in the reaction tank 101 is heated with a heating jacket 106 at the bottom. The exhaust air 109 from the reaction tank 101 goes to a cyclone 115 to trap the hemp oil entrapped in the air. The cyclone is heated with a heating jacket 116 to keep the collected hemp oil in the liquid form to be circulated back to the reaction tank 101. The air 112 left from the cyclone is cleaned with an air filter 113 to be exhausted into the air.

Figure 2:
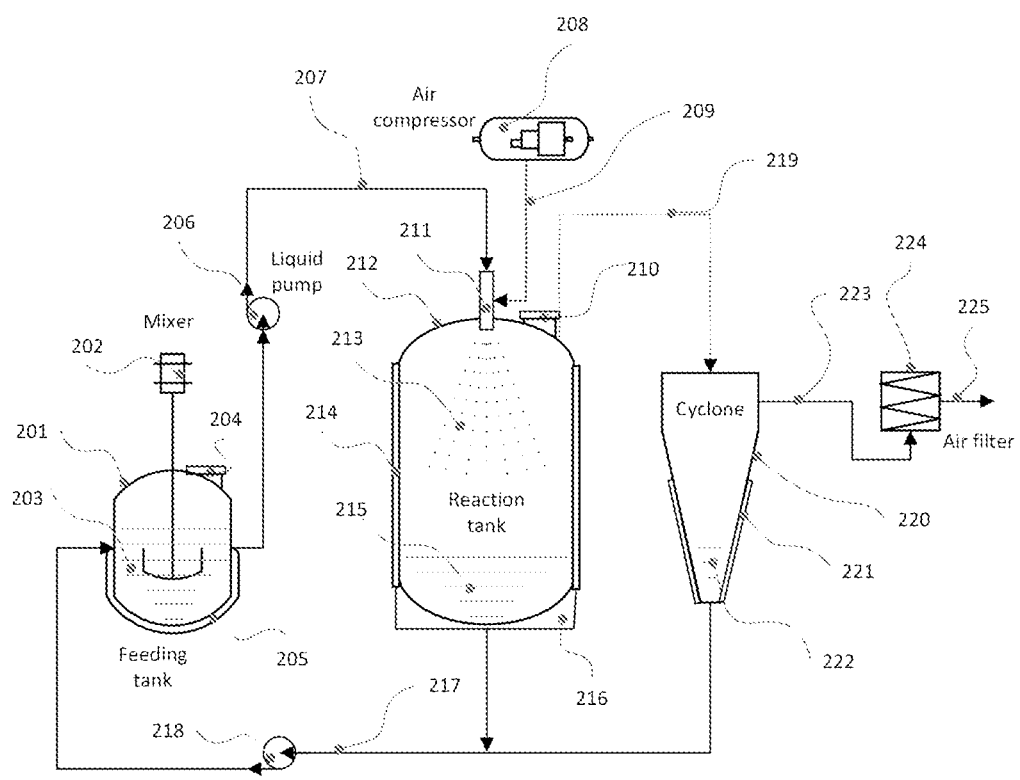
FIG. 2 is a schematic view of a semicontinuous Δ9-THC oxidation system of this disclosure.

A second embodiment is a semicontinuous reaction system to convert Δ9-THC to CBN (FIG. 2). The hemp oil is circulated between the feeding tank 201 and reaction tank 212. The system is fabricated from stainless steel, glass, or any other suitable material. The feeding tank 201 is heated with a heating jacket 205 and assisted with a mixer 202. The hemp oil 203 in the feeding tank 201 is pumped with a liquid pump 206 to a nozzle 211. The pipeline between feeding tank 201 and nozzle 211 is heated to keep the hemp oil flowing freely. Compressed air 209 supplied with an air compressor 208 meets the hemp oil in the nozzle 211, where the hemp oil is atomized and jets into fine droplets 213. In this embodiment, the wall of the reaction tank is made of glass which is transparent to UV light 214. The nozzle also provides full contact of air/oxygen with the hemp oil to expedite the oxidation process. The hemp oil 215 in the reaction tank 212 is heated with a heating jacket 216 at the bottom. The UV light has full contact with the fine hemp oil droplets 213 in the reactor. The hemp oil is circulated back to the feeding tank 201 via a liquid pump 218. The recirculation pipeline is also heated with a heating jacket to keep the oil flowing freely. The exhaust air 219 from the reaction tank 212 goes to cyclone 220 to trap the oil entrapped in the air. The cyclone is heated with a heating jacket 221 to keep the collected hemp oil in the liquid form to be circulated back to the feeding tank 201. The exhaust air 223 left from the cyclone is cleaned with an air filter 224 to be exhausted into the air.

Example 1

In this example, approximately 800 g of hemp oil with approximately 1.33% of Δ9-THC and approximately 59.24% of CBD was processed in the batch system. The recirculate rate for the hemp oil was approximately 5-10 ml/min. The air pressure was approximately 5-10 PSI. The temperatures of the pipeline and the glass reaction tank were maintained at around approximately 60° C. A combination of UV-A, UV-B, and UV-C lights totaling 180 W was used. After five days, Δ9-THC becomes approximately less than 0.43%, and the CBD content drops to approximately 54.11%. The CBN content increased from approximately 0.31% to 1.02%.

Example 2

In another example, approximately 800 g of hemp oil from the same batch as Example 1 was processed in the batch system (approximately 1.33% Δ9-THC and approximately 59.24% of CBD). The recirculate rate for the hemp oil was approximately 5-10 ml/min. The air pressure was approximately 5-10 PSI. The temperatures of the pipeline and the glass reaction tank were maintained at around approximately 60° C. Approximately 60 W of UV-B lights was used. After five days, Δ9-THC becomes approximately 0.40%, and the CBD content drops to approximately 56.65%. The CBN content increased from approximately 0.31% to approximately 1.04%.

Example 3

In another example, approximately 800 g of hemp oil from the same batch as Example 1 was processed in the batch system (approximately 1.33% Δ9-THC and approximately 59.24% of CBD). The recirculate rate for the hemp oil was approximately 5-10 ml/min. The air pressure was approximately 5-10 PSI. The temperatures of the pipeline and the glass reaction tank were maintained at around approximately 60° C. Approximately 60 W of UV-C lights was used. After five days, Δ9-THC becomes approximately 0.39%, and the CBD content drops to approximately 57.28%. The CBN content increased from approximately 0.31% to approximately 0.95%.

Example 4

In another example, approximately 800 g of hemp oil from the same batch as Example 1 was processed in the batch system (approximately 1.33% Δ9-THC and approximately 59.24% of CBD). The recirculate rate for the hemp oil was approximately 5-10 ml/min. The air pressure was approximately 5-10 PSI. The temperatures of the pipeline and the glass reaction tank were maintained at around approximately 60° C. Approximately 45 W of UV-B lights was used. After five days, Δ9-THC becomes approximately 0.59%, and the CBD content drops to approximately 56.24%. The CBN content increased from approximately 0.31% to approximately 1.31%.

Example 5

In another example, approximately 800 g of hemp oil from the same batch as Example 1 was processed in the batch system (approximately 1.33% Δ9-THC and approximately 59.24% of CBD). The recirculate rate for the hemp oil was approximately 5-10 ml/min. The air pressure was approximately 5-10 PSI. The temperatures of the pipeline and the glass reaction tank were maintained at around approximately 60° C. No UV light was used. After seven days, Δ9-THC becomes approximately 0.38%, and the CBD content drops to approximately 56.97%. The CBN content increased from approximately 0.31% to approximately 1.07%.

What is claimed is:

1. A method of oxidative conversion of Δ9-tetrahydrocannabinol (Δ9-THC) to cannabinol (CBN) in a heated spray system assisted with ultraviolet (UV) lights comprising:
   heating hemp oil in a pipeline to keep the hemp oil flowing freely in the system;
   converting Δ9-THC to CBN comprising spraying the hemp oil as droplets in the presence of oxygen and UV lights;
   recirculating the hemp oil for batch or semicontinuous operation.

2. The method of claim 1, wherein the step of converting comprises heating to assist oxidation of Δ9-THC to CBN.

3. The method of claim 1, wherein the step of converting uses air to oxidize Δ9-THC to CBN.

4. The method of claim 1, wherein the step of converting Δ9-THC to CBN utilizes pressurized air at approximately 5-30 PSI to spray the oil into droplets to expedite conversion.

5. The method of claim 1, wherein the step of converting Δ9-THC to CBN takes approximately 4-7 days.

6. The method of claim 2, wherein the hemp oil is heated to between approximately 55° C. and 100° C.

7. The method of claim 1, wherein the UV lights comprise UV-A, UV-B, UV-C, or any combination thereof.

8. The method of claim 4, wherein the heated hemp oil is sprayed into droplets via a nozzle with compressed air at approximately 5-30 PSI.

9. The method of claim 1, wherein the droplets have particle sizes of about 100-500 microns.

10. The method of claim 1, wherein the step of converting Δ9-THC to CBN, utilizes pressurized air at approximately 5-30 PSI to form the hemp oil into droplets between approximately 100 microns and 500 microns.

* * * * *